United States Patent [19]

Schally et al.

[11] Patent Number: 5,792,747
[45] Date of Patent: Aug. 11, 1998

[54] HIGHLY POTENT AGONISTS OF GROWTH HORMONE RELEASING HORMONE

[75] Inventors: Andrew V. Schally, Metairie; Jan Izdebski, New Orleans, both of La.

[73] Assignee: The Administrators of the Tulane Educational Fund, New Orleans, La.

[21] Appl. No.: 377,764

[22] Filed: Jan. 24, 1995

[51] Int. Cl.$^6$ .................................................. A61K 38/00
[52] U.S. Cl. .............................................. 514/12; 530/324
[58] Field of Search ............................ 514/12; 530/324

[56] References Cited

U.S. PATENT DOCUMENTS

| | | | |
|---|---|---|---|
| 4,689,318 | 8/1987 | Kaiser et al. | 514/12 |
| 4,914,189 | 4/1990 | Schally et al. | 530/324 |
| 5,550,212 | 8/1996 | Zarandi et al. | 530/324 |

FOREIGN PATENT DOCUMENTS

| | | |
|---|---|---|
| 0413839 | 2/1991 | European Pat. Off. . |
| 9411396 | 5/1994 | WIPO . |
| 9411397 | 5/1994 | WIPO . |

OTHER PUBLICATIONS

Zarandi et al., "Potent Agonists of growth–hormone–releasing hormone." *Int. J. Peptide Protein Res.* 39, 1992, 211–217.

*Primary Examiner*—Cecilia J. Tsang
*Assistant Examiner*—C. Delacroix-Muirheid
*Attorney, Agent, or Firm*—Omri M. Behr, Ees.

[57] ABSTRACT

Synthetic peptides which have the sequence:

$Q^1$-CO-Ala$^2$-Asp$^3$-Ala$^4$-Ile$^5$-Phe$^6$-Thr$^7$-R$^8$-Ser$^9$-Tyr$^{10}$-Arg$^{11}$-R$^{12}$-Val$^{13}$-Leu$^{14}$-R$^{15}$-Gln$^{16}$-Leu$^{17}$-Ser$^{18}$-Ala$^{19}$-Arg$^{20}$-R$^{21}$-Leu$^{22}$-Leu$^{23}$-Gln$^{24}$-Asp$^{25}$-Ile$^{26}$-R$^{27}$-R$^{28}$-NH-$Q^2$ wherein $Q^1$ is an omega or alpha-omega substituted alkyl of the structure:

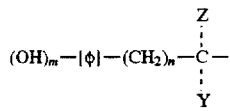

where:

[φ] is phenyl; Y is H, —NH$_2$, CH$_3$CONH— or CH$_3$NH—; Z is H or CH$_3$; m is 1 or 2; n is 0, 1 or 2; R$^8$ is Asn, Ser, Gln or Thr; R$^{12}$ is Lys or Orn; R$^{15}$ is Gly, Ala, or Abu; R$^{21}$ is Lys or Orn; R$^{27}$ is Met or Nle; R$^{28}$ is Ser or Asp; and $Q^2$ is a lower omega-guanidino-alkyl group having a formula: —(CH$_2$)$_p$—NH—C(NH$_2$)=NH wherein p is 2–6, and the pharmaceutically acceptable addition salts thereof with the pharmaceutically acceptable organic or inorganic bases or acids.

17 Claims, No Drawings

HIGHLY POTENT AGONISTS OF GROWTH HORMONE RELEASING HORMONE

This invention was made in part with Government support. The Government has certain rights in this application.

FIELD OF THE INVENTION

The present invention relates to peptides having influence on the function of the pituitary gland in humans and other animals. In particular, the present invention is directed to a synthetic peptide which promotes the release of growth hormone by the pituitary gland.

BACKGROUND OF THE INVENTION

In 1981 human pancreas growth hormone releasing hormone (hGH-RH) was isolated from extracts of human pancreatic tumors. This peptide was found to promote the release of growth hormone (GH) by the pituitary. Subsequently human hypothalamic GH-RH was characterized and found to have the same structure as pancreatic one. Human GH-RH (hGH-RH) contains 44 amino acids with an amidated carboxyl terminus. The structure of hGH-RH was reproduced by synthesis. Several analogs of hGH-RH have been synthesized and their biological activity studied. These studies revealed that:

a) a fragment of GH-RH containing at least 29 amino acid residues has at least 50% of the potency of natural GH-RH; further deletion of amino acid residues results in a marked decrease in bioactivity [Cambell et al. Peptides 12,569–574 (1991)];

b) replacement of Arg in position 29 by Agm (agmatine, 4-guanidino-butylamine) is said to provide resistance to enzymatic degradation from C-terminus (Bajusz et al. in Peptides, 1982, Blaha and Melon, Eds., Walter de Gruyter, Berlin-N.Y., 1983, pp. 643–647);

c) replacement of Tyr in position 1 by des-aminotyrosine (Dat) is said to lead to analogs with increased biological activities as a result of the resistance of N-terminus to enzymatic degradation [Felix et al. Int. J. Peptide Protein Res. 32, 441–454 (1988), Kovacs et al. Life Sci. 42, 27–35 (1988)]. U.S. Pat. Nos. 4,622,312, 4,649,131 and 4,784,987 disclose hGH-RH(1-29) agonists with Ala at position 15, as well as Dat at position 1. Several of these agonists are said to have in vitro potency four-fold that of hGH-RH(1-29).

d) several analogs containing Dat in position and Agm in position 29 are said to exhibit enhanced GH releasing ability, and hence potency greater than that of hGH-RH(1-29) in vitro and in vivo [Zarandi et al. Int. J. Peptide Protein Res. 36, 499–505 (1990), Zarandi et al. Int. J. Peptide Protein Res. 39, 211–217 (1992)].

Similarly, U.S. Pat. No. 4,914,189 discloses agonists having Dat at position 1, D-Ala at position 2, Lys or Orn at position 12, Gly at position 15, Lys at position 21 and Agm at position 29. It should be noted however that those agonists said to have had greater potency in inducing GH release than hGH-RH(1-29) had Lys at position 12 and D-Ala at position 2.

Other hGH-RH(1-29) agonists are taught in PCT patent applications numbers WO 94/11396 and 94/11397, where position 12, $Lys^{12}$, is to be replaced by D-Lys, Arg or Orn. These analogs may also contain Dat as $R^1$; Asn, D-Asn, Ser, D-Ser as $R^8$; Abu as $R^{15}$; Lys, D-Lys, Arg or D-Arg as $R^{21}$; Nle as $R^{27}$; Asp or Ser as $R^{28}$; and Agm as $R^{29}$. Those agonists which are said to induce GH at levels exceeding those induced by hGH-RH(1-29) had Lys at positions 12.

The teachings of these two publications however are considered open to question since, some time after the filing of these applications, it was discovered that the compounds believed to have been synthesized could not with certainty be said to correspond with the formulae they were originally paired with. Moreover, it was further discovered after filing these applications that the compounds could not release GH at the levels originally asserted.

European Patent Application 0 413 839 discloses further hGH-RH analogs in which positions 12 and 21 may both be Lys or Orn, and where position 15 is Ala. However, those analogs tested for GH releasing ability and said to have greater potency than hGH-RH(1-29) had Lys at positions 12 and 21. In U.S. Pat. No. 4,689,318, analogs of hGH-RH(1-29) may have $Lys^{12}$ or $Lys^{21}$ replaced by Orn and in which position 8 could be Ser, Asn, Thr or Gln; and position 27 could be Nle. In these analogs, position 1 is never Dat, position 15 never Abu, position 28 never Asp, and position 29 never Agm. Those analogs said to have potency as strong as hGH-RH(1-40) had Arg at positions 12 and 21.

When GH-RH and its analogs are incubated in serum or in homogenates of liver, pituitary and hypothalamus, GH-RH and its analogs are rapidly metabolized and the resulting shortened peptides are not biologically active. The major cleavage site in plasma is the peptide bond between residues 2 and 3 (dipeptidyl-peptidase) [Frohman et al., J. Clin. Invest. 83, 1533–1540 (1989), Kubiak et al. Drug Met. Disp. 17, 393–397 (1989)]. In pituitary and hypothalamus, the major cleavage sites are between $Leu^{14}$-$Gly^{15}$ (chymotrypsin-like enzymes) and between $Lys^{21}$-$Leu^{22}$ (trypsin-like enzymes) [Boulanger et al. Brain Res. 616, 39–47 (1993)]. Other trypsin specific cleavages at basic amino acid residues are also observed.

It would be desirable to produce hGH-RH analogs having increased resistance to enzymatic degradation as well as increased potency. However, it is not currently possible to determine what changes in three dimensional structure in a polypeptide the size of hGH-RH (1-29) result from replacing one or more amino acids, or in steric fit with biological receptors. Consequently, it is impossible to predict which one or more amino acid replacements in hGH-RH analogs might result in improved steric fit or desired resistance to degradation. Thus, the above disclosures contain no motivation to combine any particular amino acid replacements in GH-RH analogs to arrive at improved resistance to enzymatic degradation as well as increased potency.

SUMMARY OF THE INVENTION

The novel synthetic peptides of this invention exhibit surprisingly high levels of activity in stimulating the release of pituitary GH in animals, including humans. The high in vitro levels of GH stimulated by these synthetic peptides are believed to result from superior binding capacity to the hGH-RH receptor. These synthetic hGH-RH analogs also retain their physiological activity in solution for an extended period of time and resist enzymatic degradation in the body. The extremely high potency of these synthetic peptides in vivo—up to 200 times greater than that of hGH-RH(1-29)— is believed to be a function of the peptides' resisting local degradation at the injection site, as well as resisting enzyme degradation in the bloodstream. Without in any way limiting the invention or its scope, applicants wish to express their understanding that the retention of activity in vitro and resistance to in vivo degradation are due to: replacing Lys in the synthetic peptides with ornithine (Orn), which is a poor substrate for trypsin-like enzymes; incorporation of des-amino-Tyr (Dat) in position 1 which protects peptides from the degradation at the N-terminus; incorporation of agmatine (Agm) at the 29 position which protects peptides from degradation at the C-terminus; and also the replacement of Gly at residue 15 by Abu. To increase chemical stability, Met in position 27 is replaced by norleucine (Nle). Replacement of other residues in the peptides also is found to promote biological activity.

Synthetic peptides

The synthetic peptides (abbreviated |PeP|) have the sequence (SEQ ID NO: 1):

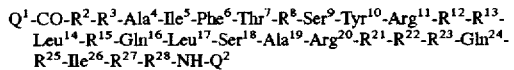

wherein $Q^1$ is an omega or alpha-omega substituted alkyl of the structure:

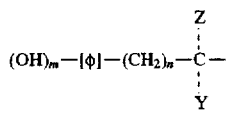

where:

|φ| is phenyl;

Y is H, —NH$_2$, CH$_3$CONH— or CH$_3$NH—;

Z is H or CH$_3$;

m is 1 or 2; and n is 0, 1 or 2;

$R^2$ is Ala, Abu or Aib;

$R^3$ is Asp or Glu;

$R^8$ is Asn, Ser, Gln or Thr;

$R^{12}$ is Lys or Orn;

$R^{13}$ is Val or Ile;

$R^{15}$ is Ala, Gly or Abu;

$R^{21}$ is Lys or Orn;

$R^{22}$ is Leu, Ala or Abu;

$R^{23}$ is Leu, Ala or Abu;

$R^{25}$ is Asp or Glu;

$R^{27}$ is Met, Nle, Ile, or Leu;

$R^{28}$ is Asp, Asn or Ser; and $Q^2$ is a lower omega-guanidino-alkyl group having a formula:

wherein p is 2–6, and the pharmaceutically acceptable addition salts thereof with the pharmaceutically acceptable organic or inorganic bases and organic or inorganic acids. Preferably, at least one of $R^{12}$ and $R^{21}$ is Orn. In certain preferred embodiments, $Q^1$—CO is Dat, $R^{15}$ is Abu, $R^{21}$ is Orn, $R^{27}$ is Nle and —NH—$Q^2$ is Agm.

(As used herein, the symbol φ signifies para-substituted phenyl, except that when used as -|φ|- wherein random, i.e., ortho, meta, para or bis-substitution is signified.)

In one preferred embodiment, the synthetic peptides of the present invention have the sequence (SEQ ID NO: 2):

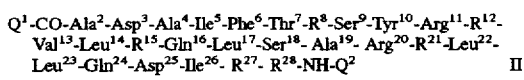

wherein $Q^1$, $R^8$, $R^{12, 15}$, $R^{21}$, $R^{27}$, $R^{28}$ and $Q^2$ are as defined above. Preferably $Q^1$—CO is Dat, $R^{15}$ is Abu, at least one of $R^{12}$ and $R^{21}$ is Orn, $R^{27}$ is Nle and —NH—$Q^2$ is Agm.

In other preferred embodiments, the synthetic peptides are (Dat$^1$, Orn$^{12,21}$,Abu$^{15}$,Nle$^{27}$,Agm$^{29}$)-hGH-RH(1-29), (Dat$^1$, Orn$^{12,21}$, Abu$^{15}$, Nle$^{27}$, Asp$^{28}$, Agm$^{29}$)hGH-RH (1-29), (Dat$^1$,Thr$^8$, Orn$^{12,21}$, Abu$^{15}$, Nle$^{27}$, Asp$^{28}$, Agm$^{29}$)hGH-RH (1-29), and (Dat$^1$, Gln$^8$, Orn$^{12,21}$, Abu$^{15}$, Nle$^{27}$, Asp$^{28}$, Agm$^{29}$)hGH-RH (1-29).

Synthetic Methods

The synthetic peptides are synthesized by a suitable method such as by exclusively solid phase techniques, by partial solid-phase techniques, by fragment condensation or by classical solution phase synthesis.

When the analogs of this invention are synthesized by solid-phase method, the C-terminal residue (here, $Q^2$) may appropriately be linked (anchored) to a suitable resin such as 4-methyl-benzylhydrylamine resin, as through the sulfenoxy acetyl group described in Zarandi et al., 1992 supra. Then, the adjacent upstream residue (i.e., the residue next closest to the N-terminal) is coupled. After completion of this coupling step, the alpha amino protecting group is removed from this newly added amino acid residue and the next amino acid (suitably protected) is added, followed by further sequential additions of amino acid residues in the C→N direction. The protecting group of each residue's alpha amino terminal moiety are removed after each residue is added, but the side chain protecting groups, (e.g., $X^2$, $X^3$ etc. in formula |PR||PeP| below) are not yet removed. After all the desired amino acids have been linked in the proper sequence, the peptide is cleaved from the support and then freed from any side chain protecting group(s) under conditions that are minimally destructive towards residues in the sequence. This must be followed by a careful purification and scrupulous characterization of the synthetic product, so as to ensure that the structure obtained is indeed the one desired.

It is particularly preferred to protect the alpha amino group of the amino acid residues during the coupling step with an acid sensitive protecting group. Such protecting groups should have the properties of being stable in the conditions of peptide linkage formation, while being readily removable without destruction of the growing peptide chain or racemization of any of the chiral centers contained therein. A suitable alpha amino protecting group is Boc.

Synthetic Intermediates

Intermediates formed during synthesis of the peptides, attached to the support phase and having protective groups which inhibit reaction by the side chains of certain amino acid residues, also constitute part of the invention.

Medical Applications

Successful treatment of growth hormone deficiency using hGH-RH and hGH-RH(1-40) has been reported in Takano K et al., Endocrinol. Japan 35; 775–781 (1988) and Thorner M. O. et al., N.Engl.J.Med., 312, 4–9 (1985) respectively. Therapeuticic treatments using hGH-RH(1-29) have also been reported against human growth hor-mone deficiency, Ross R. J. M. et al., Lancet 1:5–8, (1987); decreased GH in elderly males, Corpas et al., J. Clin. Endocrin. Metabol. 75, 530–535 (1992); and idiopathic short stature, Kirk J. M. W. et al., Clinical Endocrinol. 41, 487–493 (1994). Since earlier analogs of hGH-RH have successfully treated conditions associated with low levels of GH, it is not surprising that the novel synthetic hGH-RH peptides described herein also induce release of GH and are novel therapeutic treatments for these conditions.

Indeed, this suitability as a therapeutic agent is confirmed by the in vivo testing reported below. This testing is considered reasonably predictive of the results which one could expect in treating higher mammals, including humans. From the results below, one would expect that the novel synthetic hGH-RH analogs to be useful in therapeutically treating humans for growth hormone deficiency, as well as for a number of other conditions growing out of very low levels of GH. Thus, the invention further comprises a method of treating human growth hormone deficiency comprising administering from 0.01 μg to 2 μg of a peptide per day per kg body weight.

The synthetic peptides may be formulated in a pharmaceutical dosage form with an excipient and administered to humans or animals for therapeutic or diagnostic purposes. More particularly, the synthetic peptides may be used to promote the growth of warm-blooded animals, as, in humans, to treat human growth deficiency by stimulating in vivo synthesis and/or release of endogenous GH; to treat certain physiological conditions such as severe growth retardation due to chronic renal in-sufficiency; to offset certain effects of aging, e.g., reducing loss of muscle and bone loss; to accelerate healing and tissue repair; to improve feed utilization, thereby increasing lean/fat ratio favoring muscle gain at the cost of fat; and also to enhance milk production in lactating cattle. Further, the synthetic peptides may be used in a method to ascertain endogenous physiological ability to produce hGH.

DESCRIPTION OF THE PREFERRED EMBODIMENTS

A. SYNTHETIC PEPTIDES

1. Nomenclature

The nomenclature used to define the amino acid residues and synthetic peptides is that specified by the IUPAC-IUB Commission on Biochemical Nomenclature (*European J. Biochem.*, 1984, 138, 9–37). By natural amino acid is meant one of the common, naturally occurring amino acids found in proteins comprising Gly, Ala, Val, Leu, Ile, Ser, Thr, Lys, Arg, Asp, Asn, Glu, Gln, Cys, Met Phe, Tyr, Pro, Trp and His. By Nle is meant norleucine, by Abu is meant alpha amino butyric acid, by Orn is meant ornithine, and by Aib is meant alpha iso-butyric acid.

Other abbreviations used are:

| | |
|---|---|
| Boc- | tert-butyloxycarbonyl- |
| 2-Br-Cbz | 2-bromo-benzyloxycarbonyl- |
| Cbz- | benzyloxycarbonyl- |
| Chx- | cyclohexyl- |
| 2-Cl-Cbz- | 2-chloro-benzyloxycarbonyl- |
| DCCl | dicyclohexylcarbodiimide |
| DIC | diisopropylcarbodiimide |
| DCM | dichloromethane |
| DIEA | diisopropylethylamine |
| DMF | dimethylformamide |
| HOBt | 1-hydroxybenzotriazole |
| HPLC | high performance liquid chromatography |
| MeOH | methyl alcohol |
| TFA | trifluoroacetic acid |
| Tos- | p-toluensulfonyl- |

The amino acid sequences of the synthetic peptides are numbered in corres-pondence with the amino acid residues in hGH-RH(1-29); thus, for example, the Ala$^4$ and R$^8$ in the synthetic peptides occupy the same position in the sequence as the Ala$^4$ and R$^8$ residues in hGH-RH(1-29).

The convention under which the N-terminal of a peptide is placed to the left, and the C-terminal to the right is also followed herein. It should be understood that the terms N- and C-terminal used with respect to the synthetic peptides mean Q$^1$—CO— and —NH—Q$^2$ respectively.

2. Preferred Embodiments

Preferred embodiments of the synthetic peptides of the present invention have the sequence:

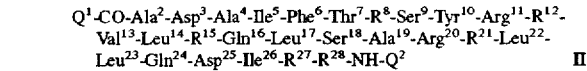

$$\text{Q}^1\text{-CO-Ala}^2\text{-Asp}^3\text{-Ala}^4\text{-Ile}^5\text{-Phe}^6\text{-Thr}^7\text{-R}^8\text{-Ser}^9\text{-Tyr}^{10}\text{-Arg}^{11}\text{-R}^{12}\text{-}$$
$$\text{Val}^{13}\text{-Leu}^{14}\text{-R}^{15}\text{-Gln}^{16}\text{-Leu}^{17}\text{-Ser}^{18}\text{-Ala}^{19}\text{-Arg}^{20}\text{-R}^{21}\text{-Leu}^{22}\text{-}$$
$$\text{Leu}^{23}\text{-Gln}^{24}\text{-Asp}^{25}\text{-Ile}^{26}\text{-R}^{27}\text{-R}^{28}\text{-NH-Q}^2 \qquad \text{II}$$

wherein Q$^1$, R$^8$, R$^{12}$, R$^{15}$, R$^{21}$, R$^{27}$, R$^{28}$ and Q$^2$ are as defined above. Preferably, Q$^1$—CO is Dat; R$^8$ is Asn, Ser, Gln or Thr; R$^{15}$ is Abu; at least one of R$^{12}$ and R$^{21}$ is Orn; R$^{27}$ is Met or Nle; R$^{28}$ is Ser or Asp; and NH—Q$^2$ is Agm. In certain preferred synthetic peptides of Formula II, Q$^1$—CO is Dat, R$^{15}$ is Abu; R$^{21}$ is Orn; R$^{27}$ is Nle; and NH—Q$^2$ forms Agm.

In one preferred analog, in Q$^1$, m is 1, n is 1 and Y and Z are H, so that Q$^1$—CO forms Dat; R$^{12}$ is Orn, R$^{15}$ is Abu, R$^{21}$ is Orn, R$^{27}$ is Nle, R$^{28}$ is Ser; and in Q$^2$, p is 4, so that —NH—Q$^2$ forms Agm, the peptide has the formula: Dat$^1$-Ala$^2$-Asp$^3$-Ala$^4$-Ile$^5$-Phe$^6$-Thr$^7$-Asn$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$- Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Ser$^{28}$-NH-(CH$_2$)$_4$-NH-C(NH$_2$)=NH. This analog may be expressed under a well known convention as follows: (Dat$^1$, Orn$^{12,21}$, Abu$^{15}$, Nle$^{27}$, Agm$^{29}$)-hGH-RH(1-29). This is the analog described in Example I below.

In another preferred synthetic peptide, Q$^1$—CO— forms Dat, R$^{12}$ is Orn, R$^{15}$ is Abu, R$^{21}$ is Orn, R$^{27}$ is Nle, R$^{28}$ is Asp; and —NH—Q$^2$ forms Agm, the peptide has the formula: Dat$^1$-Ala$^2$-Asp$^3$-Ala$^4$-Ile$^5$-Phe$^6$-Thr$^7$-Asn$^8$-Ser$^9$-Tyr$^{10}$-Arg$^{11}$-Orn$^{12}$-Val$^{13}$-Leu$^{14}$-Abu$^{15}$-Gln$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-NH-(CH$_2$)=NH, which may be abbreviated as: (Dat$^1$, Orn$^{12,21}$, Abu$^{15}$, Nle$^{27}$, Asp$^{28}$, Agm$^{29}$)hGH-RH(1-29), as described in Example IV.

In yet another preferred synthetic peptide, where Q$^1$—CO forms Dat, R$^8$ is Thr, R$^{12}$ is Orn, R$^{15}$ is Abu, R$^{21}$ is Orn, R$^{27}$ is Nle, R$^{28}$ is Asp; and —NH—Q$^2$ forms Agm, the peptide has the formula: Dat$^1$-Ala$^2$-Asp$^3$-Ala$^4$-Ile$^5$-Phe$^6$-Thr$^7$-Thr$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-NH(CH$_2$)$_4$-NH-C(CH$_2$)=NH, which may be abbreviated as: (Dat$^1$, Thr$^8$, Orn$^{12,21}$, Abu$^{15}$, Nle$^{27}$, Asp$^{28}$, Agm$^{29}$)hGH-RH(1-29), as described in Example V.

Similarly, where Q$^1$—CO is Dat, R$^8$ is Gln, R$^{12}$ is Orn, R$^{15}$ is Abu, R$^{21}$ is Orn, R$^{27}$ is Nle, R$^{28}$ is Asp; and Q$^2$ forms Agm, the peptide has the formula: Dat$^1$-Ala$^2$-Asp$^3$-Ala$^4$Ile$^5$-Phe$^6$-Thr$^7$-Gln$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-NH-(CH$_2$)=NH, which may be abbreviated as: (Dat$^1$, Gln$^8$, Orn$^{12,21}$, Abu$^{15}$, Nle$^{27}$, Asp$^{28}$, Agm$^{29}$)hGH-RH(1-29), as described in Example VI.

B. SYNTHETIC METHODS

1. Overview of Synthesis

The peptides are synthesized by a suitable method such as by exclusively solid phase techniques, by partial solid-phase techniques, by fragment condensation or by classical solution phase synthesis. For example, the techniques of exclusively solid-phase synthesis are set forth in the textbook "Solid Phase Peptide Synthesis", J. M. Stewart and J. D. Young, Pierce Chem. Company, Rockford, Ill., 1984 (2nd. ed.), G. Barany and R. B. Merrifield, "The Peptides", Ch. 1, 1–285, pp. 1979, Academic Press, Inc., and M. Bodanszky, "Principles of Peptide Synthesis", Springer Verlag, 1984. The synthetic peptides are preferably prepared using solid phase synthesis, such as that generally described by Merrifield, J.Am.Chem.Soc., 85, 2149 (1963), although other equivalent chemical syntheses known in the art can also be used as previously mentioned.

In solid phase synthesis, it is suitable to join the moiety which forms the C or N-terminal moiety of the resulting peptide to a polymeric resin support phase via a chemical link. The other amino acid residues or oligopeptide fragments are then added sequentially to this C or N-terminal moiety until the desired peptide sequence is obtained. Because the amino acid residues or oligopeptide fragments are added to the C-terminal $Q^2$ group here, growth of the synthetic peptides begins at the C terminal and progresses toward the N-terminal. When the desired sequence has been obtained, it is removed from the support phase.

When one or more of the various amino acid moieties or peptide fragments have reactive side chain functional groups, suitable protecting groups prevent a chemical reaction from occurring at said side chains until the protecting group is ultimately removed. Accordingly, it is common that, as a step in synthesis, an intermediate compound is produced which includes each of the amino acid residues located in its desired sequence in the peptide chain with side-chain protecting groups linked to the appropriate residues.

2. Joining $NH_2$—$Q^2$ to the Support Phase

A variety of support phases are suitable for synthesizing the synthetic peptides. These support phases may be amino- or hydroxy-type resins such as amino-methyl resins (suitably 1% cross linked), benzhydrylamine resins (suitably 2% cross linked) p-methylbenzhydrylamine resins (suitably 2% cross linked) and the like. It is generally preferred that the support phase [SP] is an amino type resin of the formula: $H_2N$—$CH_2$-φ-[Pm] where [Pm] is a polymeric substrate.

The initial material joined to the support phase is suitably the C-terminal $Q^2$ group. Preferably, the adjacent —NH— functional group is already affixed to $Q^2$. Agm or 4-guanidino butylamine are especially preferred.

The —NH—$Q^2$ group is joined to the support phase via a stable but readily cleavable bridging group. It has been found that such a bridge may be readily provided by a sulfonyl phenoxy acetyl moiety. Thus, Boc-NH-$Q^2$-$SO_2$-φ-(M$_s$)O-$CH_2$-CO [SP] may suitably constitute the material joined to the support phase for the synthetic sequence. It is prepared and linked to the support phase as described in Zarandi et al., 1992 supra and U.S. Pat. No. 4,914,189, both incorporated by reference herein.

3. Stepwise Addition of Amino Acid Residues

Utilizing the aforementioned Boc-protected amino-alkyl-guanidino sulfophenoxyacetyl as the anchored C-terminal, the peptide itself may then suitably be built up by solid phase synthesis in the conventional manner. Thus, the alpha amino-protecting group of the next amino acid residue, $R^{28}$, is protected by Boc to prevent reaction between the C-terminal carboxyl group and alpha amino groups of $R^{28}$. The $R^{28}$ moiety is attached to $H_2N$-$Q^2$-$SO_2$-[φ](M$_s$)-O-$CH_2$-COOH. The remaining amino acid residues of the synthetic peptides are added sequentially, with $Q^1$—CO finally being added. Because the peptide is constructed from the C-terminal, the residues are added in reverse numerical order, i.e., $R^{28}$, $R^{27}$, and so forth. As an alternative to adding each amino acid separately in the synthesis, some may be coupled to one another in a separate vessel and added as an oligopeptide in the solid phase reaction.

Each protected amino acid or amino acid sequence is introduced into the solid phase reaction in about a three-fold molar excess, with respect to a compound being acylated and the coupling may be carried out in as medium such as DMF: $CH_2Cl_2$ or in DMF or $CH_2Cl_2$ alone. The selection of an appropriate coupling reagent is within the skill of the art.

Particularly suitable as coupling reagents are N,N'-dicyclohexylcarbodiimide(DCCl); N,N'-diisopropylcarbodiimide (DIC); and the BOP carboxyl activating reagent. In cases where incomplete coupling occurs, the coupling procedure is repeated before removal of the alpha amino protecting group prior to the coupling of the next amino acid. The success of the coupling reaction at each stage of the synthesis is preferably monitored by the ninhydrin reaction.

4. Removal of Complete Intermediate from the Support Phase

When the synthesis is complete, the $Q^2$ guanidino alkyl end of the synthetic peptide is cleaved from the support phase at the sulfonyl group. Removal of the intermediate peptide from the resin support is performed by treatment with liquid hydrogen fluoride. This also cleaves all the side chain protecting groups from the side chains of the amino acid residues.

C. SYNTHETIC INTERMEDIATES

1. Side Chain Protecting Groups

The protection of reactive side chain functional groups of the various amino acid moieties or peptide fragments is common to solid phase synthesis. These side chain functional groups are protected in order to prevent these side chains from par-ticipating in undesirable chemical reactions. Accordingly, it is common that, as a step in the synthesis, an intermediate compound is produced which includes each of the amino acid residues located in its desired sequence in the peptide chain with side-chain protecting groups (e.g., $X^1$, $X^7$, etc.) linked to the appropriate residues.

The selection of a side chain amino protecting group is not critical except that generally one is chosen which is not removed by the deprotection of the alpha amino groups during synthesis. In selecting a particular side chain protecting group to be used in the synthesis of the peptides, the following general rules are followed: (a) the protecting group preferably retains its protecting properties and is not split off under coupling conditions, (b) the protecting group should be stable to the reagent and the coupling reaction conditions selected for removing the alpha amino protecting group at each step of the synthesis, and (c) the protecting group must be removable upon the completion of the synthesis of the desired amino acid sequence, under reaction conditions that will not undesirably alter the peptide chain. The side chain protecting groups are attached to the amino acid residues by steps well known in the art.

2. Synthetic Intermediates

Also considered to be within the scope of the present invention are intermediates of the formula: [PR] [PeP] attached to a support phase [SP] selected from the group consisting of amino-type resins, said combination having the structure:

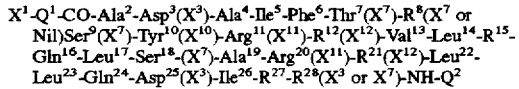

[PR][PeP]-SO$_2$-[φ](M$_s$)-O-CH$_2$-CO-SP where M is hydrogen, lower alkyl or lower alkoxy of 1 to 5 carbon atoms, suitably methyl or methoxy, s is 1–3, and [SP] is an amino type resin. Suitably [PR][PeP] has the structure:

$X^1$-$Q^1$-CO-Ala$^2$-Asp$^3$($X^3$)-Ala$^4$-Ile$^5$-Phe$^6$-Thr$^7$($X^7$)-R$^8$($X^7$ or Nil)Ser$^9$($X^7$)-Tyr$^{10}$($X^{10}$)-Arg$^{11}$($X^{11}$)-R$^{12}$($X^{12}$)-Val$^{13}$-Leu$^{14}$-R$^{15}$-Gln$^{16}$-Leu$^{17}$-Ser$^{18}$-($X^7$)-Ala$^{19}$-Arg$^{20}$($X^{11}$)-R$^{21}$($X^{12}$)-Leu$^{22}$-Leu$^{23}$-Gln$^{24}$-Asp$^{25}$($X^3$)-Ile$^{26}$-R$^{27}$-R$^{28}$($X^3$ or $X^7$)-NH-Q$^2$ wherein $X^1$ is either hydroxyl, or an amino protecting group or nil, depending on the meaning of Y;

$X^3$ is a suitable ester-forming protecting group for the carboxyl group of Asp or Glu, such as cyclohexyl esters;

$X^7$ is a suitable protecting group for the hydroxyl group of Thr or Ser, such as Bzl;

$X^{10}$ is a suitable protecting group for the phenolic hydroxyl group of Tyr such as 2Br-Cbz;

$X^{11}$ is a suitable protecting group for the guanidino group of Arg, such as Tos; and $X^{12}$ is a suitable protecting group for the side chain amino group of Lys or Orn.

2-chloro-benzyloxycarbonyl (2-Cl-CBz) is illustrative of suitable side chain amino protecting groups.

D. MEDICAL APPLICATIONS

The products of the present invention may be utilized to promote the growth of warm-blooded animals (e.g., humans) and also enhance the milk production of females of milk producing mammals, suitably but not exclusively goats and cows, preferably cows.

The peptides of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, citrate, benzoate, succinate, alginate, pamoate, malate, ascorbate, tartrate, and the like.

The compounds of the present invention are suitably administered to the subject humans or animals s.c., i.m., or i.v; intranasally or by pulmonary inhalation; or in a depot form (e.g., microcapsules, microgranules, or cylindrical rod like implants) formulated from a biodegradable suitable polymer (such as D,L-lactide-co-glycolide), the former two depot modes being preferred. Other equivalent modes of administration are also within the scope of this invention, i.e., continuous drip, depot injections, infusion pump and time release modes such as microcapsules and the like. Administration is in any physiologically acceptable injectable carrier, physiological saline being acceptable, though other carriers known to the art may also be used.

The dosage level is suitably between 0.01 µg and 2 µg per kg body weight per injection, except for depot form where the amount injected would be calculated to last from about 15 to about 30 days or longer. These dosage ranges are merely preferred. Administration of non-depot forms may be between 1 and 4 times per day, or in the case of lactating mammals, after each milking.

Until the production of growth hormone by recombinant-DNA methods began, the small supply of pituitary-derived human growth hormone limited its use to the treatment of children with growth hormone deficiency. The wide availability of synthetic human growth hormone has made possible long-term studies of other potentially beneficial uses of growth hormone and its more physiologic actions. Although synthetic GH is currently approved in the USA only for treatment of growth failure due to lack of endogenous growth hormone, this therapy has also been used to treat short children not classically GH deficient. However the cost of long-term treatment with hGH and the need of daily s.c. administration are important considerations. Currently, the cost of growth hormone therapy for a child with growth deficiency ranges from $10,000 to 30,000 a year depending on body weight. Treatment of a 70-kg adult with hGH three times a week costs $13,800 a year. Vance, M. L., N.Eng.J.Med 323:52-54 (1990). Thus, long-term growth hormone treatment in elderly adults with diminished growth hormone secretion would require a considerable personal and financial investment. In addition there are many children all over the world with growth retardation due to the lack of GH who cannot be treated with hGH because of the cost of this therapy. Consequently there is an urgent need to develop a drug that releases GH and with an affordable price. This alternative method to increase endogenous growth hormone secretion is through the administration of agonistic analogs of growth hormone-releasing hormone. The therapy with GH-RH agonistic analogs should be much less expensive than that utilizing hGH. In addition, the development of long-acting delivery systems for these analogs can make this new modality of treatment more practical and convenient.

The ability to produce synthetic growth hormone by recombinant DNA technology has enabled the manufacture of GH in potentially unlimited quantities. This greatly facilitated the treatment of GH-deficient children. As stated above, synthetic hGH is currently approved only for the treatment of growth failure due to a lack of adequate endogenous growth hormone, but hGH has also been used to treat short children who are not classically GH-deficient such as girls with Turner's syndrome; prepubertal children with chronic renal insufficiency and severe growth retardation; and children with non-GH deficient short stature.

Of the 3 million children born in the USA annually, 90,000 will be below the third percentile for height. These children may be labeled as having short stature and may be candidates for GH treatment. Therapy with human growth hormone currently costs about $20,000 per year and the average length of treatment is about 10 years. The treatment will usually be stopped when the patient reaches an acceptable adult size (a height of well over five feet) or when the patient matures sexually and the epiphyses close, at which time linear growth eases, or if the patient fails to respond to the treatment. If all children who are less than the third percentile for height receive a five year course of hGH therapy, hGH for height augmentation therapy will cost at least $8 billion to 10 billion per year. Lantos J. et al., JAMA 261:1020-1024, (1989).

It is desirable to ascertain the endogenous physiological ability of children having short stature to produce hGH. This may be done with a diagnostic test using a 50-100 µg dose of GH-RH; a 50-100 microgram dose of a GH-RH analog which is a synthetic peptide of Formula I; and assaying the GH response evoked by each dose.

The assay means may be any conventional means which will indicate the quantitative amount of hGH present in a blood sample drawn from the patient. The concentration of GH in serum is determined using standard radioimmunoassay ("RIA") procedures as set forth in e.g., Miles I. E. M. et al., Lancet ii, 492-493 (1968) or O'Dell W et al., J.Lab.-Clin.Med. 70, 973-80 (1967).

The test is used as follows. First, the GH-RH dose is administered. Thirty minutes later, a blood sample is taken for RIA of GH. Various commercially available kits (e.g., Nichols Institute of Diagnostics, San Juan Capistrano, Calif.) or reference preparations of hGH (e.g., NIAMDD-hGH-RP-1) can be used for RIA of GH. After waiting 6-24 hours for the effect of GH-RH to wear off, the dose of the synthetic peptide GH-RH analog is administered. Blood again is drawn for radioimmunoassay of GH.

The presence of a normal hGH response in the first assay reveals that endogenous hGH producing ability is present. This result also suggests a short, mild course of GH-RH therapy, if any, may be suitable. A low GH response, or no response, to the first dose reveals only that GH-RH must be evaluated in view of the second test result. If a good hGH response follows the second dose, there is clear physiological hGH producing ability which is not evoked by GH-RH.

This indicates that a therapy with the GH-RH analog may be desirable. Finally, no or low response to both tests reliably reveals lack of physiological ability to produce hGH, and so suggests therapy with hGH is probably needed.

As indicated above, short stature in children may result from many causes, none of which are immediately apparent. Use of the diagnostic test on all children with this condition would greatly clarify the cause of short stature. Such a widespread screening test would also provide earlier indications for desirable treatment.

Glucocorticoids are potent inhibitors of linear growth in man and growth suppression is a well known risk of long term treatment of asthmatic children with steroids. Thus stunted growth is an important consequence of chronic administration of glucocorticoids in childhood. The inhibition of GH secretion is due in some extent to the fact that chronic administration of glucocorticoids suppresses GHRH. This inhibition occurs at the level of the hypothalamus or above and in this situation only the treatment with GH-RH agonists will stimulate linear growth.

Growth hormone tends to decline with the aging process and may lead to decrease in muscle mass and adiposity. Studies have shown that healthy older men and women with growth hormone deficiency had increases in lean body mass and decreases in the mass of adipose tissue after six months of hGH administration. Other effects of long-term administration of hGH on body composition included increase in vertebral-bone density and increase in skin-fold thickness. In addition, it has been reported that daily GH-RH injection to menopausal women, for 8 days augments GH responses and IGF-I levels and raises serum osteocalcin levels. Thus the therapy with GH-RH agonistic analogs reduces the loss of muscle, bone and skin mass and lessen the increase of body fat that normally accompanies the aging process.

Growth hormone is a potent anabolic hormone that enhances protein synthesis and nitrogen retention. Chronic administration of agonistic analogs of GH-RH increases the endogenous growth hormone secretion. The therapy with GH-RH agonistic analogs has uses in other areas of medicine such as catabolic states causing accelerated weight loss; tissue repair in patients with severe body surface burn, accelerating healing of nonunion fractures; and in some cases of cardiac failure.

Although long term follow-up is necessary before all treatment responses can be ascribed to GH, there has been improvement in cardiac mass and an increase in both cardiac mass and contractility. The therapy with hGH interrupts the cardiac-cachexia cycle. This response is in keeping with other observations that the therapy with GH has a major role in catabolic states in adults. An alternative method to increase endogenous growth hormone secretion in these conditions is the administration of GH-RH agonistic analogs. Korpas et al., J. Clin. Endoc. Metabol. 75, 530–535, (1992).

These agonistic analogs of GH-RH can replace hGH for many applications. GH-deficient children respond to GH-RH(1-40), GH-RH(1-29) or GH-RH(1-44), with an increase in growth. Thorner M. O. et al., supra; Ross et al., supra; Takano K et al., supra; and Kirk et al., supra. Most children who respond to hGH, will respond to GH-RH. This is because most GH-deficient children have a hypothalamic defect in GH release, and will show a GH response after the administration of analogs of the hypothalamic hormone GH-RH. Thus repeated administration of GH-RH promotes linear growth. GH-RH(1-29)NH$_2$ given subcutaneously twice a day promoted linear growth in approximately 50% of a group of GH-deficient children (Ross et al. cited above). A small group of severely GH-deficient children will respond to GH-RH after 6 (six) months of treatment.

FURTHER CLINICAL APPLICATIONS OF AGONISTIC ANALOGS OF GH-RH IN CHILDREN WITH GROWTH RETARDATION

1. As a screening test for growth hormone deficiency
2. Treatment of Hypothalamic GH-RH deficiency
3. Constitutional growth delay
4. Turner Syndrome
5. Familial short stature
6. Prepubertal children with chronic renal insufficiency and severe growth retardation
7. Infants and children with intrauterine growth retardation
8. Children with GH deficiency following radiotherapy for pituitary or hypothalamic lesions
9. Children on long-term treatment with glucocorticoids and growing at subnormal rate

FURTHER CLINICAL APPLICATIONS OF AGONISTIC ANALOGS OF GH-RH IN ADULTS

1. Geriatric Patients: To reduce the loss of muscle, bone and skin mass and lessen the increase of body fat that normally accompanies the aging process.
2. Catabolic states
3. Wound healing
4. Delayed healing of fractures
5. Osteoporosis
6. Obesity
7. As an adjunct to total parenteral nutrition in malnourished patients with chronic obstructive pulmonary disease
8. Cardiac failure
9. GH-RH agonists could be used during and after space flights to counteract the decrease in GH secretion. Weightlessness of space flight significantly decreases the release of growth hormone, which could explain the bone loss and muscle weakness many astronauts experience after prolonged space flights.

The following Examples set forth suitable methods for synthesizing several of the synthetic GH-RH analog peptides by the solid-phase technique. As noted above, steps which are suitable for initial synthesis of these synthetic peptides are disclosed in Examples I through VII of U.S. Pat. No. 4,914,189.

EXAMPLE I $(Dat^1, Orn^{12,21}, Abu^{15}, Nle^{27}, Agm^{29})hGH-RH(1-29)$

The synthesis of an hGH-RH analog of the formula (SEQ ID NO: 3): $Dat^1$-$Ala^2$-$Asp^3$-$Ala^4$-$Ile^5$-$Phe^6$-$Thr^7$-$Asn^8$-$Ser^9$-$Tyr^{10}$-$Arg^{11}$-$Orn^{12}$-$Val^{13}$-$Leu^{14}$-$Abu^{15}$-$Gln^{16}$-$Leu^{17}$-$Ser^{18}$-$Ala^{19}$-$Arg^{20}$-$Orn^{21}$-$Leu^{22}$-$Leu^{23}$-$Gln^{24}$-$Asp^{25}$-$Ile^{26}$-$Nle^{27}$-$Ser^{28}$-$Agm^{29}$ is carried out in a stepwise manner on a PS-2755 (Protein Technologies) automatic synthesizer or manually starting with the appropriate Boc-NH-$(CH_2)_4$-NH-$C(NH_2)=N$-$\phi$-$OCH_2$-CO-[SP] in accordance with the procedures set forth below in the Schedules.

Deblocking and neutralization are preferably carried out in accordance with Schedule as follows:

SCHEDULE, deprotection

| Step | Reagent | Mixing time (min) |
|---|---|---|
| 1. | Deprotect: TFA:DCM (50:50) | 2 + 15 |
| 2. | Wash: DCM (2X) | 1 |
| 3. | Wash: 25% dioxane in DCM (2X) | 1 |
| 4. | Wash: DCM (2X) | 1 |
| 5. | Neutralization: 5% DIEA in DCM (2X) | 2 |
| 6. | Wash: DCM (6X) | 1 |

The couplings are preferably carried out as set out in the Schedule for coupling:

SCHEDULE, coupling

| Step | Reagent | Mixing time (min) |
|---|---|---|
| 1. | Coupling: preformed symmetrical anhydride of Boc-amino acid (3 equ.) (or preformed HOBt ester) in DCM or DCM + DMF | 60 |
| 2. | Washing: DCM (6X) | 1 |

The couplings are preferably carried out in DCM alone or DCM+DMF mixture (Gln, Leu, Arg and Orn) with 3 equivalents of symmetrical anhydrides of Boc-amino acids, or preformed HOBt esters of Boc-amino acids. Asn is coupled with the use of preformed HOBt ester of Boc-Asn. For the formation of activated compounds, N,N'-dicyclohexylcarbodiimide or N,N'-diisopropylcarbodiimide are used.

Briefly, a Boc group is used to protect the alpha amino group of the amino acid residue being coupled. Benzyl ether is used as the hydroxyl side protecting group for Ser and Thr. The phenolic hydroxyl group of Tyr is protected by 2-Br-Cbz, the phenolic hydroxyl group of Dat is protected by Cbz. The side chain carboxyl group of Asp is protected in the form of a cyclohexyl ester. Tos is used to protect the guanidino group of Arg and 2-Cl-Cbz is used as the protecting group of the Orn side chain amino group. Thus, the resulting peptide-resin bears Chx at $Asp^{3,25}$, Bzl at $Thr^7$ and $Ser^{9,18,28}$, 2-Cl-Cbz at $Orn^{12,21}$, 2-Br-Cbz at $Tyr^{10}$, Cbz at $Dat^1$, and Tos at $Arg^{11,20}$.

In order to cleave and deprotect the peptide-resin, a sample of peptide-resin (0.1–1 g) is treated with 1 ml of anisol and 10 ml of hydrogen fluoride (HF) at 0° for 45–60 min. The HF is removed with a rapid stream of nitrogen at 0° over 15 min. The residue is washed with dry diethyl ether and ethyl acetate. The peptide is then extracted with 50% aqueous acetic acid, separated from the resin by filtration and lyophilized.

The crude peptide is purified using a Rabbit HPLC system (Rainin Instrument Co. Inc., Woburn, Mass.) equipped with a Knauer UV Photometer and Kipp and Zonen BD 40 Recorder and a 10×250 mm VYDAC C18 column (300 Å pore size, 5 μm particle size). The column is eluted with a solvent system consisting of (A) 0.1% aqueous TFA and (B) 0.1% TFA in 70% aqueous MeCN in a linear gradient mode (e.g. from 30 to 70% B in 50 min), flow rate 2 ml/min. Fractions are analyzed on a Hewlett-Packard HP-1090 liquid chromatograph equipped with a 4.6×250 mm VYDAC C18 column (5 μm) at a flow rate 1.2 ml/min and gradient from 40 to 70% B in 30 min. Homogeneous fractions (one peak) are combined, diluted with water and lyophilized.

EXAMPLE II $(Dat^1,Abu^{15},Orn^{21},Nle^{27},Agm^{29})hGH-RH(1-29)$

The synthesis of an hGH-RH analog of the formula (SEQ ID NO: 4):

$Dat^1$-$Ala^2$-$Asp^3$-$Ala^4$-$Ile^5$-$Phe^6$-$Thr^7$-$Asn^8$-$Ser^9$-$Tyr^{10}$-$Arg^{11}$-$Lys^{12}$-$Val^{13}$-$Leu^{14}$-$Abu^{15}$-$Gln^{16}$-$Leu^{17}$-$Ser^{18}$-$Ala^{19}$-$Arg^{20}$-$Orn^{21}$-$Leu^{22}$-$Leu^{23}$-$Gln^{24}$-$Asp^{25}$-$Asp^{25}$-$Ile^{26}$-$Nle^{27}$-$Ser^{28}$-$Agm^{29}$ was carried out as described in Example I, to give another protected peptide-resin having the formula: $Dat^1(Cbz)$-$Ala^2$-$Asp^3(OChx)$-$Ala^4$-$Ile^5$-$Phe^6$-$Thr^7(Bzl)$-$Asn^8$-$Ser^9(Bzl)$-$Tyr^{10}(2$-$Br$-$Cbz)$-$Arg^{11}$-$(Tos)$-$Lys^{12}(2$-$Cl$-$Cbz)$-$Val^{13}$-$Leu^{14}$-$Abu^{15}$-$Gln^{16}$-$Leu^{17}$-$Ser^{18}$-$(Bzl)$-$Ala^{16}$-$Arg^{20}(Tos)Orn^{21}(2$-$Cl$-$Cbz)$-$Leu^{22}$-$Leu^{23}$-$Gln^{24}$- $Asp^{25}$ $(OChx)$-$Ile^{26}$-$Nle^{27}$-$Ser^{28}(Bzl)$-$NH$-$(CH^2$-$)_4$-$NH$-$C(NH_2)=$ $N$-$|SPA|$-$|SP|$. Thus, the resulting peptide-resin bears Chx at $Asp^{3,25}$, Bzl at $Thr^7$ and $Ser^{9,18,28}$, 2-Cl-Cbz at $Orn^{21}$ and $Lys^{12}$, 2-Br-Cbz at $Tyr^{10}$, Cbz at $Dat^1$, and Tos at $Arg^{11,20}$. This peptide-resin is then similarly converted to the desired peptide in accordance with the procedure of Example I.

EXAMPLE III $(Dat^1,Orn^{12},Abu^{15},Nle^{27},Agm^{29})hGH-RH(1-29)$

The synthesis of an hGH-RH analog of the formula (SEQ ID NO:10): $Dat^1$-$Ala^2$-$Asp^3$-$Ala^4$-$Ile^5$-$Phe^6$-$Thr^7$-$Asn^8$-$Ser^9$-$Tyr^{10}$-$Arg^{11}$-$Orn^{12}$-$Val^{13}$-$Leu^{14}Abu^{15}$-$Gln^{16}$-$Leu^{17}$-$Ser^{18}$-$Ala^{19}$-$Arg^{20}$-$Lys^{21}$-$Leu^{22}$-$Leu^{23}$-$Gln^{24}$-$Asp^{25}$-$Ile^{26}$-$Nle^{27}$-$Ser^{28}$-$Agm^{29}$ was carried out as described in Example I, to give another protected peptide-resin having the formula: $Dat^1(Cbz)$-$Ala^2$-$Asp^3(OChx)$-$Ala^4$-$Ile^5$-$Phe^6$-$Thr^7$ $(Bzl)$-$Asn^8$-$Ser^9(Bzl)$-$Tyr^{10}(2$-$Br$-$Cbz)$-$Arg^{11}(Tos)$-$Orn^{12}(2$-$Cl$-$Cbz)$-$Val^{13}$-$Leu^{14}$-$Abu^{15}$-$Gln^{16}$-$Leu^{17}$-$Ser^{18}(Bzl)$-$Ala^{19}$-$Arg^{20}(Tos)$-$Lys^{21}(2$-$Cl$-$Cbz)$-$Leu^{22}$-$Leu^{23}$-$Gln^{24}$-$Asp^{25}$ $(OChx)$-$Ile^{26}$-$Nle^{27}$-$Ser^{28}(Bzl)$-$NH$-$(CH_2)_4$-$NH$-$C(NH_2)=$ $N$-$|SPA|$-$[SP]$. Thus, the resulting peptide resin bears Chx at $Asp^{3,25}$, Bzl at $Thr^7$ and $Ser^{9,18,28}$, 2-Cl-Cbz at $Orn^{12}$ and $Lys^{21}$, 2-Br-Cbz at $Tyr^{10}$, Cbz at $Dat^1$, and Tos at $Arg^{11,20}$. This peptide-resin is then similarly converted to the desired peptide in accordance with the procedure of Example I.

EXAMPLE IV $(Dat^1,Orn^{12,21},Abu^{15},Nle^{27},Asp^{28},Agm^{29})hGH$-$RH$ (1-29)

The synthesis of an hGH-RH analog of the formula (SEQ ID NO: 5): $Dat^1$-$Ala^2$-$Asp^3$-$Ala^4$-$Ile^5$-$Phe^6$-$Thr^7$-$Asn^8$-$Ser^9$-$Tyr^{10}$-$Arg^{11}Orn^{12}$-$Val^{13}$-$Leu^{14}$-$Abu^{15}$-$Gln^{16}$-$Leu^{17}$-$Ser^{18}$-$Ala^{19}$-$Arg^{20}Orn^{21}$-$Leu^{22}$-$Leu^{23}$-$Gln^{24}$-$Asp^{25}$-$Ile^{26}$-$Nle^{27}$-$Asp^{28}$-$Agm^{29}$ was carried out as described in Example I, to give another protected peptide-resin having the formula:

$Dat^1(Cbz)$-$Ala^2$-$Asp^3(OChx)$-$Ala^4$-$Ile5$-$Phe^6$-$Thr^7(Bzl)$-$Asn^8$-$Ser^9(Bzl)$-$Tyr^{10}$-$(2$-$Br$-$Cbz)$-$Arg^{11}(Tos)$-$Orn^{12}(2$-$Cl$-$Cbz)$-$Val^{13}$-$Leu^{14}$-$Abu^{15}$-$Gln^{16}$-$Leu^{17}$-$Ser^{18}(Bzl)$-$Ala^{19}$-$Arg^{20}(Tos)$-$Orn^{21}(2$-$Cl$-$Cbz)$-$Leu^{22}$-$Leu^{23}$-$Gln^{24}$-$Asp^{28}(Chx)$-$NH$-$(CH_2)_4$-$NH$-$C$-$(NH_2)=N$-$[SPA]$-$[SP]$

Thus, the resulting peptide-resin bears Chx at $Asp^{3,25,28}$, Bzl at $Thr^7$ and $Ser^{9,18}$, 2-Cl-Cbz at $Orn^{12,21}$, 2-Br-Cbz at $Tyr^{10}$, Cbz at $Dat^1$, and Tos at $Arg^{11,20}$. This peptide-resin is then similarly converted to the desired peptide in accordance with the procedure of Example I.

EXAMPLE V $(Dat^1,Thr^8,Orn^{12,21},Abu^{15},Nle^{27},Asp^{28},Agm^{29})hGH$-$RH(1-29)$

The synthesis of an hGH-RH analog of the formula (SEQ ID NO: 6): $Dat^1$-$Ala^2$-$Asp^3$-$Ala^4$-$Ile^5$-$Phe6$-$Thr^7$-$Thr^8$-$Ser^9$-$Tyr^{10}$-$Arg^{11}$-$Orn^{12}$- $Val^{13}$-$Leu^{14}$-$Abu^{15}$-$Gln^{16}$-$Leu^{17}$-$Ser^{18}$-$Ala^{19}$-$Arg^{20}$-$Orn^{21}$-$Leu^{22}Leu^{23}$-$Gln^{24}$-$Asp^{25}$-$Ile^{26}$-$Nle^{27}$-

Asp$^{28}$-Agm$^{29}$ was carried out as described in Example I, to give another protected peptide-resin having the formula: Dat$^1$(Cbz)-Ala$^2$-Asp$^3$(OChx)-Ala$^4$-Ile$^5$-Phe$^6$-Thr$^7$(Bzl)-Thr$^8$(Bzl)-Ser$^9$(Bzl)-Tyr$^{10}$(2-Br-Cbz)-Arg$^{11}$(Tos)-Orn$^{12}$-(2-Cl-Cbz)-Val$^{13}$-Leu$^{14}$-Abu$^{15}$-Gln$^{16}$-Leu$^{17}$-Ser$^{18}$(Bzl)-Ala$^{19}$-Arg$^{20}$-(Tos)-Orn$^{21}$-(2-Cl-Cbz)-Leu$^{22}$-Leu$^{23}$-Gln$^{24}$-Asp$^{25}$(OChx)-Ile$^{26}$-Nle$^{27}$-Asp$^{28}$(Chx)-NH-(CH$_2$)$_4$-NH-C(NH$_2$)=N-|SPA|-|SP|. Thus, the resulting peptide-resin bears Chx at Asp$^{3,25,28}$, Bzl at Thr$^{7,8}$ and Ser$^{9,18}$, 2-Cl-Cbz at Orn$^{12,21}$, 2-Br-Cbz at Try$^{10}$, Cbz at Dat$^1$, and Tos at Arg$^{11,20}$. This peptide-resin is then similarly converted to he desired peptide in accordance with the procedure of Example I.

EXAMPLE VI (Dat$^1$,Gln$^8$,Orn$^{12,21}$,Abu$^{15}$,Nle$^{27}$,Asp$^{28}$,Agm$^{29}$) hGH-RH(1-29)

The synthesis of an hGH-RH analog of the formula (SEQ ID NO: 7): Dat$^1$-Ala$^2$-Asp$^3$-Ala$^4$-Ile$^5$-Phe$^6$-Thr$^7$-Gln$^8$-Ser$^9$-Tyr$^{10}$-Arg$^{11}$-Orn$^{12}$-Val$^{13}$-Leu$^{14}$-Abu$^{15}$-Gln$^{16}$- Leu$^{17}$-Ser$^{18}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-Agm$^{29}$ was carried out as described in Example I, to give another protected peptide-resin having the formula: Dat$^1$(Cbz)-Ala$^2$-Asp$^3$(OChx)-Ala$^4$-Ile$^5$-Phe$^6$-Thr$^7$(Bzl)-Gln$^8$-Ser$^9$(Bzl)-Tyr$^{10}$(2-Br-Cbz)-Arg$^{11}$(Tos)-Orn$^{12}$(2-Cl-Cbz)-Val$^{13}$-Leu$^{14}$-Abu$^{15}$-Gln$^{16}$-Leu$^{17}$-Ser$^{18}$(Bzl)-Ala$^{19}$-Arg$^{20}$(Tos)-Orn$^{21}$(2-Cl-Cbz)-Leu$^{22}$-Leu$^{23}$-Gln$^{24}$-Asp$^{25}$(OChx)-Ile$^{26}$-Nle$^{27}$-Asp$^{28}$(Chx)-NH-(CH$_2$)$_4$-NH-C(NH$_2$)=N-|SPA|-[SP]. Thus, the resulting peptide-resin bears Chx at Asp$^{3,25,28}$, Bzl at Thr$^7$ and Ser$^{9,18}$, 2-Cl-Cbz at Orn$^{12,21}$, 2-Br-Cbz at Tyr$^{10}$, Cbz at Dat, and Tos at Arg$^{11,20}$. This peptide-resin is then similarly converted to the desired peptide in accordance with the procedure of Example I.

EXAMPLE VII (Dat$^1$,Ser$^8$,Orn$^{12,21}$,Abu$^{15}$,Nle$^{27}$,Agm$^{29}$)hGH-RH(1-29)

The synthesis of an hGH-RH analog of the formula (SEQ ID NO: 8): Dat$^1$-Ala$^2$-Asp$^3$-Ala$^4$-Ile$^5$-Phe$^6$-Thr$^7$-Ser$^8$-Ser$^9$-Tyr$^{10}$-Arg$^{11}$Orn$^{12}$-Val$^{13}$-Leu$^{14}$- Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Ser$^{28}$-Agm$^{29}$ was carried out as described in Example I, to give another protected peptide-resin having the formula: Dat$^1$(Cbz)-Ala$^2$-Asp$^3$(OChx)-Ala$^4$-Ile$^5$-Phe$^6$-Thr$^7$(Bzl)-Ser$^8$(Bzl)-Ser$^9$(Bzl)-Tyr$^{10}$(2-Br-Cbz)-Val$^3$-Leu$^{14}$-Abu$^{15}$-Gln$^{16}$-Leu$^{17}$-Ser$^{18}$(Bzl)-Ala$^{19}$Arg$^{20}$(Tos)-Orn$^{21}$(2-Cl-Cbz)-Leu$^{22}$-Leu$^{23}$-Gln$^{24}$-Asp$^{25}$(OChx)-Ile$^{26}$-Nle$^{27}$Ser$^{28}$(Bzl)-NH-(CH$_2$)$_4$-NH-C(NH$_2$)=N-[SPA]-[SP]. Thus the resulting peptide-resin bears Chx at Asp$^{3,25}$, Bzl at Thr$^7$ and Ser$^{8,9,18,28}$, 2-Cl-Cbz at Orn$^{12,21}$, 2-Br-Cbz at Tyr$^{10}$, Cbz at Dat$^1$, and Tos at Arg$^{11,20}$. This peptide-resin is then similarly converted to the desired peptide in accordance with the procedure of Example I.

EXAMPLE VIII (Dat$^1$,Gln$^8$,Orn$^{12,21}$,Abu$^{15}$,Nle$^{27}$,Agm$^{29}$)hGH-RH(1-29)

The synthesis of an hGH-RH analog of the formula (SEQ ID NO: 9): Dat$^1$-Ala$^2$-Asp$^3$-Ala$^4$-Ile$^5$-Phe$^6$-Thr$^7$-Gln$^8$-Ser$^9$-Tyr$^{10}$-Arg$^{11}$-Orn$^{12}$-Val$^{13}$-Leu$^{14}$- Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Ser$^{28}$-Agm$^{29}$ was carried out as described in Example I, to give another protected peptide-resin having the formula: Dat$^1$(Cbz)-Ala$^2$-Asp$^3$(OChx)-Ala$^4$-Ile$^5$-Phe$^6$-Thr$^7$(Bzl)-Gln$^8$-Ser$^9$(Bzl)-Tyr$^{10}$(2-Br-Cbz)-Arg$^{11}$(Tos)-Orn$^{12}$(2-Cl-Cbz)-Val$^{13}$-Leu$^{14}$-Abu$^{15}$-Gln$^{16}$-Leu$^{17}$-Ser$^{18}$(Bzl)-Ala$^{19}$-Arg$^{20}$(Tos)-Orn$^{21}$(2-Cl-Cbz)-Leu$^{22}$-Leu$^{23}$-Gln$^{24}$-Asp$^{25}$(OChx)-Ile$^{26}$Nle$^{27}$-Ser$^{28}$(Bzl)-NH-(CH$_2$)$_4$-NH-C(NH$_2$)=N-|SPA|-|SP|. Thus, the resulting peptide-resin bears Chx at Asp3,25, Bzl at Thr$^7$ and Ser$^{9,18,28}$, 2-Cl-Cbz at Orn$^{12,21}$, 2-Br-Cbz at Tyr$^{10}$, Cbz at Dat$^1$, and Tos at Arg$^{11,20}$. This peptide-resin is then similarly converted to the desired peptide in accordance with the procedure of Example I.

Test Procedures

The compounds of the present invention were tested both in vitro and in vivo. The levels of growth hormone released by the synthetic peptides in vitro are summarized in Table 1. The levels of GH released in vivo by the synthetic peptides, following their intravenous (i.v.) or subcutaneous (sc.) injection in rats, are shown in Tables 2 and 3 respectively. The potencies of the peptides, based on 4-point assays, were calculated in all the Examples of this specification, by the factorial analyses of Bliss and Marks with 95% confidence limits.

EXAMPLE IX

Growth hormone releasing activity in vitro is assayed by using a superfused rat pituitary cell system as described in S. Vigh and A. V. Schally, Peptides 5, Suppl: 241–347, 1984, which is incorporated by reference herein. Each peptide, hGH-RH (1-29)NH$_2$ (as control) and the synthetic peptide hGH-RH analogs of the present invention, is administered for 3 minutes (1 ml. perfusate) at various concentrations as shown below. Fractions of 1 ml are collected and the GH content in each is determined by RIA.

TABLE 1

In vitro effect of hGH-RH analogs (0.1–0.5 nM) on the GH release in superfused rat pituitary cell system

| Peptide | Potency relative to hGH-RH(1–29)NH$_2$ = 1 |
|---|---|
| Example I | 5.9 |
| Example II | 6.4 |
| Example III | 3.8 |

EXAMPLE X—Intravenous Administration

For in vivo tests based on intravenous administration, adult male Sprague-Dawley rats are anesthetized with pentobarbital (6 mg./100/g., b.w.), injected i.p.; 20 minutes after the injection of pentobarbital, blood samples are taken from the jugular vein (pretreated level) and immediately thereafter hGH-RH (1-29)NH$_2$ (as a control) or hGH-RH(1-29)NH$_2$ analogs are injected i.v. Blood samples are taken from the jugular vein 5 and 15 minutes after the injection. The blood samples are centrifuged, plasma is removed and the GH level is measured by RIA. The results expressed as potency relative to hGH-RH(1-29)NH$_2$ appear in Table 2.

TABLE 2

Potency of hGH-RH analogs in vivo relative to hGH-RH(1–29)NH$_2$ (= 1) in the rat after i.v. injection

| hGH-RH Analog | After (min) | Potency |
|---|---|---|
| Example I | 5 | 3.8 |
|  | 15 | 6.1 |
| Example II | 5 | 3.0 |
|  | 15 | 5.2 |

TABLE 2-continued

Potency of hGH-RH analogs in vivo relative to hGH-RH(1–29)NH$_2$ (= 1) in the rat after i.v. injection

| hGH-RH Analog | After (min) | Potency |
|---|---|---|
| Example III | 5 | 1.2 |
| | 15 | 4.5 |

EXAMPLE XI—Subcutaneous Administration

Adult male rats are used and are anesthetized with pentobarbital (6 mg/100 g., b.w.), injected i.p.; 20 minutes after the injection of pentobarbital, blood samples are taken from the jugular vein (pretreated level) and immediately thereafter hGH-RH(1-29)NH$_2$ (as a control) or hGH-RH analogs are injected subcutaneously (s.c.). Blood samples are taken from the jugular vein 15 and 30 minutes after the injection. The blood samples are centrifuged, plasma is removed and the GH level is measured by RIA. The results are summarized in terms of potency in Table 3.

TABLE 3

Potency of hGH-RH analogs in vivo after subcutaneous (s.c.) injection relative to hGH-RH(1–29)NH$_2$ (= 1)

| hGH-RH analog | After (min) | Potency |
|---|---|---|
| Example I | 15 | 44.6 |
| | 30 | 217.7 |
| Example II | 15 | 13.9 |
| | 30 | 60.2 |
| Example III | 15 | 17.3 |
| | 30 | 89.5 |

TABLE 3-continued

Potency of hGH-RH analogs in vivo after subcutaneous (s.c.) injection relative to hGH-RH(1–29)NH$_2$ (= 1)

| hGH-RH analog | After (min) | Potency |
|---|---|---|
| Example IV | 15 | 80.9 |
| | 30 | 89.7 |
| Example V | 15 | 95.8 |
| | 30 | 87.9 |
| Example VI | 15 | 71.4 |
| | 30 | 116.8 |
| Example VII | 15 | 22.9 |
| | 30 | 35.7 |
| Example VIII | 15 | 38.8 |
| | 30 | 108.5 |

Following intravenous administration, the analogs give growth hormone levels greater than those from hGH-RH(1-29)NH$_2$ alone. The effect is long lasting which indicates that the analogs have not only higher receptor affinity but increased peptidase resistance too. Following subcutaneous administration, again all of the analogs give greater growth hormone levels than hGH-RH. Here the analogs from Examples I, IV, V and VI produce unusually good results with a prolonged release rate.

The in vitro and in vivo results show different biological activity pattern. It is believed that in vitro activity depends primarily on binding capacity of the peptide to its receptor, whereas in vivo potency is believed to stem from favorable transport properties, suitable binding to plasma proteins and metabolic stability. The above find-ings therefore indicate that the analogs tested are resistant to local degradation at the injection site and they may also be less susceptible to enzyme degradation in the blood stream and/or have more affinity for GH-RH receptors than hGH-RH(1-29)NH$_2$.

We claim:

1. A peptide having the formula:

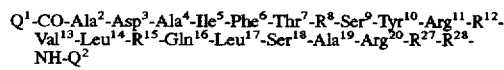

SEQ ID NO: 1 wherein $Q^1$ is an omega or alpha-omega substituted alkyl of the structure:

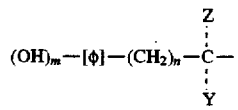

where:

[φ] is phenyl;
Y is H, —NH$_2$, CH$_3$CONH— or CH$_3$NH—;
Z is H or CH$_3$;
m is 1 or 2; and n is 0, 1 or 2;
$R^8$ is Asn, Ser, Gln or Thr;
$R^{12}$ is Orn;
$R^{15}$ is Gly, Ala, or Abu;
$R^{21}$ is Orn;
$R^{27}$ is Met or Nle;
$R^{28}$ is Ser or Asp;
$Q^2$ is a lower omega-guanidino-alkyl group having a formula:

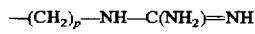

wherein p is 2–6, and at least one of $R^{12}$ and $R^{21}$ is Orn, and the pharmaceutically acceptable addition salts thereof with the pharmaceutically acceptable organic or inorganic bases or acids.

2. The peptide of Seq. ID No.: 2 having the formula:

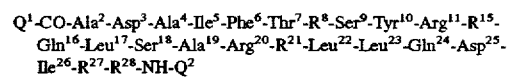

wherein $Q^1$—CO is Dat,
$R^8$ is Asn, Ser, Gln or Thr;
$R^{12}$ is Orn;
$R^{15}$ is Abu;
$R^{21}$ is Orn;
$R^{27}$ is Nle;
$R^{28}$ is Ser or Asp;
and —NH—$Q^2$ is Agm and the pharmaceutically acceptable addition salts thereof with the pharmaceutically acceptable organic or inorganic bases or acids.

3. A peptide according to claim 2 wherein $R^8$ is Asn, Ser or Gln; and $R^{28}$ is Ser.

4. A peptide according to claim 3 wherein $R^8$ is Asn.

5. A peptide according to claim 2 wherein $R^{28}$ is Asp.

6. A peptide according to claim 5 wherein $R^8$ is Asn.

7. A peptide according to claim 5 wherein $R^8$ is Gln.

8. A peptide according to claim 5 wherein $R^8$ is Thr.

9. A peptide selected from the group consisting of:

$Dat^1-Ala^2-Asp^3-Ala^4-Ile^5-Phe^6-Thr^7-Asn^8-Ser^9-Tyr^{10}-Arg^{11}-Orn^{12}-Val^{13}-Leu^{14}-Abu^{15}-Gln^{16}-Leu^{17}-Ser^{18}-Ala^{19}-Arg^{20}-Orn^{21}-Leu^{22}-Leu^{23}-Gln^{24}-Asp^{25}-Ile^{26}-Nle^{27}-Ser^{28}-Agm^{29}$ SEQ ID NO: 2;

$Dat^1-Ala^2-Asp^3-Ala^4-Ile^5-Phe^6-Thr^7-Asn^8-Ser^9-Tyr^{10}-Arg^{11}-Orn^{12}-Val^{13}-Leu^{14}-Abu^{15}-Gln^{16}-Leu^{17}-Ser^{18}-Ala^{19}-Arg^{20}-Orn^{21}-Leu^{22}-Leu^{23}-Gln^{24}-Asp^{25}-Ile^{26}-Nle^{27}-Asp^{28}-Agm^{29}$ SEQ ID NO: 5;

$Dat^1-Ala^2-Asp^3-Ala^4-Ile^5-Phe^6-Thr^7-Thr^8-Ser^9-Tyr^{10}-Arg^{11}-Orn^{12}-Val^{13}-Leu^{14}-Abu^{15}-Gln^{16}-Leu^{17}-Ser^{18}-Ala^{19}-Arg^{20}-Orn^{21}-Leu^{22}-Leu^{23}-Gln^{24}-Asp^{25}-Ile^{26}-Nle^{27}-Asp^{28}-Agm^{29}$ SEQ ID NO: 6;

$Dat^1-Ala^2-Asp^3-Ala^4-Ile^5-Phe^6-Thr^7-Gln^8-Ser^9-Tyr^{10}-Arg^{11}-Orn^{12}-Val^{13}-Leu^{14}-Abu^{15}-Gln^{16}-Leu^{17}-Ser^{18}-Ala^{19}-Arg^{20}-Orn^{21}-Leu^{22}-Leu^{23}-Gln^{24}-Asp^{25}-Ile^{26}-Nle^{27}-Asp^{28}-Agm^{29}$ SEQ ID NO: 7;

$Dat^1-Ala^2-Asp^3-Ala^4-Ile^5-Phe^6-Thr^7-Ser^8-Ser^9-Tyr^{10}-Arg^{11}-Orn^{12}-Val^{13}-Leu^{14}-Abu^{15}-Gln^{16}-Leu^{17}-Ser^{18}-Ala^{19}-Arg^{20}-Orn^{21}-Leu^{22}-Leu^{23}-Gln^{24}-Asp^{25}-Ile^{26}-Nle^{27}-Ser^{28}-Agm^{29}$ SEQ ID NO: 8 and $Dat^1-Ala^2-Asp^3-Ala^4-Ile^5-Phe^6-Thr^7-Gln^8-Ser^9-Tyr^{10}-Arg^{11}-Orn^{12}-Val^{13}-Leu^{14}-Abu^{15}-Gln^{16}-Leu^{17}-Ser^{18}-Ala^{19}-Arg^{20}-Orn^{21}-Leu^{22}-Leu^{23}-Gln^{24}-Asp^{25}-Ile^{26}-Nle^{27}-Ser^{28}-Agm^{29}$ SEQ ID NO: 9.

10. A peptide according to claim 9 having the formula:

$Dat^1-Ala^2-Asp^3-Ala^4-Ile^5-Phe^6-Thr^7-Asn^8-Ser^9-Tyr^{10}-Arg^{11}Orn^{12}-Val^{13}-Leu^{14}-Abu^{15}-Gln^{16}-Leu^{17}-Ser^{18}-Ala^{19}-Arg^{20}-Orn^{21}-Leu^{22}Leu^{23}-Gln^{24}-Asp^{25}-Ile^{26}-Nle^{27}-Ser^{28}-Agm^{29}$ SEQ ID NO: 2.

11. A peptide according to claim 9 having the formula:

$Dat^{1-Ala2}-Asp^3-Ala^4-Ile^5-Phe^6-Thr^7-Asn^8-Ser^9-Tyr^{10}-Arg^{11}Orn^{12}-Val^{13}-Leu^{14}-Abu^{15}-Gln^{16}-Leu^{17}-Ser^{18}-Ala^{19}-Arg^{20}-Orn^{21}-Leu^{22}-Leu^{23}-Gln^{24}-Asp^{25}-Ile^{26}-Nle^{27}-Asp^{28}-Agm^{29}$ SEQ ID No: 5.

12. A peptide according to claim 9 having the formula:

$Dat^1-Ala^2-Asp^3-Ala^4-Ile^5-Phe^6-Thr^7-Thr^8-Ser^9-Tyr^{10}-Arg^{11}-Orn^{12}-Val^{13}-Leu^{14}-Abu^{15}-Gln^{16}-Leu^{17}-Ser^{18}-Ala^{19}-Arg^{20}-Arg^{20}-Orn^{21}-Leu^{22}-Leu^{23}-Gln^{24}-Asp^{25}-Ile^{26}-Nle^{27}-Asp^{28}-Agm^{29}$ SEQ ID NO: 6.

13. A peptide according to claim 9 having the formula:

$Dat^1-Ala^2-Asp^3-Ala^4-Ile^5-Phe^6-Thr^7-Gln^8-Ser^9-Tyr^{10}-Arg^{11}-Orn^{12}-Val^{13}-Leu^{14}-Abu^{15}-Gln^{16}-Leu^{17}-Ser^{18}-Ala^{19}-Arg^{20}-Orn^{21}-Leu^{22}-Leu^{23}-Gln^{24}-Asp^{25}-Ile^{26}-Nle^{27}-Asp^{28}-Agm^{29}$ SEQ ID NO: 7.

14. A peptide according to claim 9 having the formula:

$Dat^1-Ala^2-Asp^3-Ala^4-Ile^5-Phe^6-Thr^7-Ser^8-Ser^9-Tyr^{10}-Arg^{11}-Orn^{12}-Val^{13}-Leu^{14}-Abu^{15}-Gln^{16}-Leu^{17}-Ser^{18}-Ala^{19}-Arg^{20}-Orn^{21}-Leu^{22}-Leu^{23}-Gln^{24}-Asp^{25}-Ile^{26}-Nle^{27}-Ser^{28}-Agm^{29}$ SEQ ID NO: 8.

15. A peptide according to claim 9 having the formula:

$Dat^1-Ala^2-Asp^3-Ala^4-Ile^5-Phe^6-Thr^7-Gln^8-Ser^9-Tyr^{10}-Arg^{11}-Orn^{12}-Val^{13}-Leu^{14}-Abu^{15}-Gln^{16}-Leu^{17}-Ser^{18}-Ala^{19}-Arg^{20}-Orn^{21}-Leu^{22}-Leu^{23}-Gln^{24}-Asp^{25}-Ile^{26}-Nle^{27}-Ser^{28}-Agm^{29}$ SEQ ID NO: 9.

16. A pharmaceutical dosage form comprising a peptide according to claim 1 and an excipient.

17. A method of treating human growth hormone deficiency comprising ad-ministering from 0.01 µg to 2 µg of a peptide according to claim 1 per day per kg body weight.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( D ) OTHER INFORMATION: /note= "Res 1 = Q1-CO- where Q1 = 3-(5- hydroxyindolyl)-methyl or an omega or alpha-omega substituted alkyl"

( i x ) FEATURE:
        ( A ) NAME/KEY: Peptide
        ( D ) OTHER INFORMATION: /note= "Res 2 = Ala, Abu or Aib"

( i x ) FEATURE:
        ( A ) NAME/KEY: Peptide
        ( D ) OTHER INFORMATION: /note= "Res 3 = Asp or Glu"

( i x ) FEATURE:
        ( A ) NAME/KEY: Peptide ( D ) OTHER INFORMATION: /note= "Res 8 = Asn, Ser, Gln or Thr"

( i x ) FEATURE:
    ( A ) NAME/KEY: Peptide
    ( D ) OTHER INFORMATION: /note= "Res 12 = Lys or Orn"

( i x ) FEATURE:
    ( A ) NAME/KEY: Peptide
    ( D ) OTHER INFORMATION: /note= "Res 13 = Val or Ile"

( i x ) FEATURE:
    ( A ) NAME/KEY: Peptide
    ( D ) OTHER INFORMATION: /note= "Res 15 = Ala, Gly or Abu"

( i x ) FEATURE:
    ( A ) NAME/KEY: Peptide
    ( D ) OTHER INFORMATION: /note= "Res 21 = Lys or Orn"

( i x ) FEATURE:
    ( A ) NAME/KEY: Peptide
    ( D ) OTHER INFORMATION: /note= "Res 22 = Leu, Ala or Abu"

( i x ) FEATURE:
    ( A ) NAME/KEY: Peptide
    ( D ) OTHER INFORMATION: /note= "Res 23 = Leu, Ala or Abu"

( i x ) FEATURE:
    ( A ) NAME/KEY: Peptide
    ( D ) OTHER INFORMATION: /note= "Res 25 = Asp or Glu"

( i x ) FEATURE:
    ( A ) NAME/KEY: Peptide
    ( D ) OTHER INFORMATION: /note= "Res 27 = Met, Nle, Ile or Leu"

( i x ) FEATURE:
    ( A ) NAME/KEY: Peptide
    ( D ) OTHER INFORMATION: /note= "Res 28 = Asp, Asn or Ser"

( i x ) FEATURE:
    ( A ) NAME/KEY: Peptide
    ( D ) OTHER INFORMATION: /note= "Res 29 = NH-Q2, where Q2 = a
        lower omega- guanidino-alkyl"

( x i ) SEQUENCE DESCRIPTION: SEQ ID NO:1:

```
Xaa Xaa Xaa Ala Ile Phe Thr Xaa Ser Tyr Arg Xaa Xaa Leu Xaa Gln
1               5                   10                  15

Leu Ser Ala Arg Xaa Xaa Xaa Gln Xaa Ile Xaa Xaa Xaa
            20                  25
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( D ) OTHER INFORMATION: /note= "Res 1 = Dat, Ac-Tyr, N-Me-Tyr,
            C-Me-Tyr, or Tyr"

( i x ) FEATURE:
        ( A ) NAME/KEY: Peptide
        ( D ) OTHER INFORMATION: /note= "Res 8 = Asn, Ser, Gln or Thr"

( i x ) FEATURE:
        ( A ) NAME/KEY: Peptide
        ( D ) OTHER INFORMATION: /note= "Res 12 = Lys or Orn"

( i x ) FEATURE:
        ( A ) NAME/KEY: Peptide
        ( D ) OTHER INFORMATION: /note= "Res 15 = Ala, Gly or Abu"

( i x ) FEATURE:

(A) NAME/KEY: Peptide
(D) OTHER INFORMATION: /note= "Res 21 = Lys or Orn"

(ix) FEATURE:
(A) NAME/KEY: Peptide
(D) OTHER INFORMATION: /note= "Res 27 = Met, Nle, Ile or Leu"

(ix) FEATURE:
(A) NAME/KEY: Peptide
(D) OTHER INFORMATION: /note= "Res 28 = Asp, Asn or Ser"

(ix) FEATURE:
(A) NAME/KEY: Peptide
(D) OTHER INFORMATION: /note= "Res 29 = NH-Q2, where Q2 = a lower omega- guanidino-alkyl"

(xi) SEQUENCE DESCRIPTION: SEQ ID NO:2:

Xaa Ala Asp Ala Ile Phe Thr Xaa Ser Tyr Arg Xaa Val Leu Xaa Gln
1               5                   10                  15

Leu Ser Ala Arg Xaa Leu Leu Gln Asp Ile Xaa Xaa Xaa
            20                  25

(2) INFORMATION FOR SEQ ID NO:3:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(D) OTHER INFORMATION: /note= "Res 1 = Dat"

(ix) FEATURE:
(A) NAME/KEY: Peptide
(D) OTHER INFORMATION: /note= "Res 12 = Orn"

(ix) FEATURE:
(A) NAME/KEY: Peptide
(D) OTHER INFORMATION: /note= "Res 15 = Abu"

(ix) FEATURE:
(A) NAME/KEY: Peptide
(D) OTHER INFORMATION: /note= "Res 21 = Orn"

(ix) FEATURE:
(A) NAME/KEY: Peptide
(D) OTHER INFORMATION: /note= "Res 27 = Nle"

(ix) FEATURE:
(A) NAME/KEY: Peptide
(D) OTHER INFORMATION: /note= "Res 29 = Agm"

(xi) SEQUENCE DESCRIPTION: SEQ ID NO:3:

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Xaa
            20                  25

(2) INFORMATION FOR SEQ ID NO:4:

(i) SEQUENCE CHARACTERISTICS:
(A) LENGTH: 29 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide (D) OTHER INFORMATION: /note= "Res 1 = Dat"

(ix) FEATURE:
  (A) NAME/KEY: Peptide
  (D) OTHER INFORMATION: /note= "Res 15 = Abu"

(ix) FEATURE:
  (A) NAME/KEY: Peptide
  (D) OTHER INFORMATION: /note= "Res 21 = Orn"

(ix) FEATURE:
  (A) NAME/KEY: Peptide
  (D) OTHER INFORMATION: /note= "Res 27 = Nle"

(ix) FEATURE:
  (A) NAME/KEY: Peptide
  (D) OTHER INFORMATION: /note= "Res 29 = Agm"

(xi) SEQUENCE DESCRIPTION: SEQ ID NO:4:

Xaa Ala Asp Ala Ile Phe Thr Asn Ser Tyr Arg Lys Val Leu Xaa Gln
1               5                   10                  15

Leu Ser Ala Arg Xaa Leu Leu Gln Asp Ile Xaa Ser Xaa
            20              25

(2) INFORMATION FOR SEQ ID NO:5:

(i) SEQUENCE CHARACTERISTICS:
    (A) LENGTH: 29 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (D) OTHER INFORMATION: /note= "Res 1 = Dat"

(ix) FEATURE:
    (A) NAME/KEY: Peptide
    (D) OTHER INFORMATION: /note= "Res 12 = Orn"

(ix) FEATURE:
    (A) NAME/KEY: Peptide
    (D) OTHER INFORMATION: /note= "Res 15 = Abu"

(ix) FEATURE:
    (A) NAME/KEY: Peptide
    (D) OTHER INFORMATION: /note= "Res 21 = Orn"

(ix) FEATURE:
    (A) NAME/KEY: Peptide
    (D) OTHER INFORMATION: /note= "Res 27 = Nle"

(ix) FEATURE:
    (A) NAME/KEY: Peptide
    (D) OTHER INFORMATION: /note= "Res 29 = Agm"

(xi) SEQUENCE DESCRIPTION: SEQ ID NO:5:

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Xaa
            20              25

(2) INFORMATION FOR SEQ ID NO:6:

(i) SEQUENCE CHARACTERISTICS:
    (A) LENGTH: 29 amino acids
    (B) TYPE: amino acid
    (C) STRANDEDNESS: single
    (D) TOPOLOGY: linear (ii) MOLECULE TYPE: peptide ( i x ) FEATURE:
    ( A ) NAME/KEY: Peptide
    ( D ) OTHER INFORMATION: /note= "Res 1 = Dat"

( i x ) FEATURE:
    ( A ) NAME/KEY: Peptide
    ( D ) OTHER INFORMATION: /note= "Res 12 = Orn"

( i x ) FEATURE:
    ( A ) NAME/KEY: Peptide
    ( D ) OTHER INFORMATION: /note= "Res 15 = Abu"

( i x ) FEATURE:
    ( A ) NAME/KEY: Peptide
    ( D ) OTHER INFORMATION: /note= "Res 21 = Orn"

( i x ) FEATURE:
    ( A ) NAME/KEY: Peptide
    ( D ) OTHER INFORMATION: /note= "Res 27 = Nle"

( i x ) FEATURE:
    ( A ) NAME/KEY: Peptide
    ( D ) OTHER INFORMATION: /note= "Res 29 = Agm"

( x i ) SEQUENCE DESCRIPTION: SEQ ID NO:6:

```
Xaa Ala Asp Ala Ile Phe Thr Thr Ser Tyr Arg Xaa Val Leu Xaa Gln
 1               5                  10                      15

Leu Ser Ala Arg Xaa Leu Leu Gln Asp Ile Xaa Asp Xaa
             20                  25
```

( 2 ) INFORMATION FOR SEQ ID NO:7:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( D ) OTHER INFORMATION: /note= "Res 1 = Dat"

( i x ) FEATURE:
    ( A ) NAME/KEY: Peptide
    ( D ) OTHER INFORMATION: /note= "Res 12 = Orn"

( i x ) FEATURE:
    ( A ) NAME/KEY: Peptide
    ( D ) OTHER INFORMATION: /note= "Res 15 = Abu"

( i x ) FEATURE:
    ( A ) NAME/KEY: Peptide
    ( D ) OTHER INFORMATION: /note= "Res 21 = Orn"

( i x ) FEATURE:
    ( A ) NAME/KEY: Peptide
    ( D ) OTHER INFORMATION: /note= "Res 27 = Nle"

( i x ) FEATURE:
    ( A ) NAME/KEY: Peptide
    ( D ) OTHER INFORMATION: /note= "Res 29 = Agm"

( x i ) SEQUENCE DESCRIPTION: SEQ ID NO:7:

```
Xaa Ala Asp Ala Ile Phe Thr Gln Ser Tyr Arg Xaa Val Leu Xaa Gln
 1               5                  10                      15

Leu Ser Ala Arg Xaa Leu Leu Gln Asp Ile Xaa Asp Xaa
             20                  25
```

( 2 ) INFORMATION FOR SEQ ID NO:8:

( i ) SEQUENCE CHARACTERISTICS:
        ( A ) LENGTH: 29 amino acids ( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( D ) OTHER INFORMATION: /note= "Res 1 = Dat"

( i x ) FEATURE:
( A ) NAME/KEY: Peptide
( D ) OTHER INFORMATION: /note= "Res 12 = Orn"

( i x ) FEATURE:
( A ) NAME/KEY: Peptide
( D ) OTHER INFORMATION: /note= "Res 15 = Abu"

( i x ) FEATURE:
( A ) NAME/KEY: Peptide
( D ) OTHER INFORMATION: /note= "Res 21 = Orn"

( i x ) FEATURE:
( A ) NAME/KEY: Peptide
( D ) OTHER INFORMATION: /note= "Res 27 = Nle"

( i x ) FEATURE:
( A ) NAME/KEY: Peptide
( D ) OTHER INFORMATION: /note= "Res 29 = Agm"

( x i ) SEQUENCE DESCRIPTION: SEQ ID NO:8:

```
Xaa Ala Asp Ala Ile Phe Thr Ser Ser Tyr Arg Xaa Val Leu Xaa Gln
1               5                   10                  15
Leu Ser Ala Arg Xaa Leu Leu Gln Asp Ile Xaa Ser Xaa
            20                  25
```

( 2 ) INFORMATION FOR SEQ ID NO:9:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( D ) OTHER INFORMATION: /note= "Res 1 = Dat"

( i x ) FEATURE:
( A ) NAME/KEY: Peptide
( D ) OTHER INFORMATION: /note= "Res 12 = Orn"

( i x ) FEATURE:
( A ) NAME/KEY: Peptide
( D ) OTHER INFORMATION: /note= "Res 15 = Abu"

( i x ) FEATURE:
( A ) NAME/KEY: Peptide
( D ) OTHER INFORMATION: /note= "Res 21 = Orn"

( i x ) FEATURE:
( A ) NAME/KEY: Peptide
( D ) OTHER INFORMATION: /note= "Res 27 = Nle"

( i x ) FEATURE:
( A ) NAME/KEY: Peptide
( D ) OTHER INFORMATION: /note= "Res 29 = Agm"

( x i ) SEQUENCE DESCRIPTION: SEQ ID NO:9:

```
Xaa Ala Asp Ala Ile Phe Thr Gln Ser Tyr Arg Xaa Val Leu Xaa Gln
1               5                   10                  15
Leu Ser Ala Arg Xaa Leu Leu Gln Asp Ile Xaa Ser Xaa
            20                  25
```

( 2 ) INFORMATION FOR SEQ ID NO:10:

( i ) SEQUENCE CHARACTERISTICS:
      ( A ) LENGTH: 29 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( D ) OTHER INFORMATION: /note= "Res 1 = Dat"

( i x ) FEATURE:
      ( A ) NAME/KEY: Peptide
      ( D ) OTHER INFORMATION: /note= "Res 12 = Orn"

( i x ) FEATURE:
      ( A ) NAME/KEY: Peptide
      ( D ) OTHER INFORMATION: /note= "Res 15 = Abu"

( i x ) FEATURE:
      ( A ) NAME/KEY: Peptide
      ( D ) OTHER INFORMATION: /note= "Res 27 = Nle"

( i x ) FEATURE:
      ( A ) NAME/KEY: Peptide
      ( D ) OTHER INFORMATION: /note= "Res 29 = Agm"

( x i ) SEQUENCE DESCRIPTION: SEQ ID NO:10:

```
Xaa Ala Asp Ala Ile Phe Thr Asn Ser Tyr Arg Xaa Val Leu Xaa Gln
 1               5                  10                  15
Leu Ser Ala Arg Lys Leu Leu Gln Asp Ile Xaa Ser Xaa
            20                  25
```